United States Patent [19]

Mayfield et al.

[11] Patent Number: 5,023,174

[45] Date of Patent: Jun. 11, 1991

[54] **RECOMBINANT *BRUCELLA ABORTUS* GENE EXPRESSING IMMUNOGENIC PROTEIN**

[75] Inventors: John E. Mayfield; Louisa B. Tabatabai, both of Ames, Iowa

[73] Assignee: Iowa State University Research Foundation, Ames, Iowa

[21] Appl. No.: 365,226

[22] Filed: Jun. 12, 1989

Related U.S. Application Data

[63] Continuation-in-part of Ser. No. 905,297, Sep. 8, 1986, abandoned.

[51] Int. Cl.⁵ .................... C12P 6/34; C12N 15/00; C07H 15/12
[52] U.S. Cl. .................... 435/91; 435/317.1; 435/320.1; 536/27
[58] Field of Search ............... 435/68, 91, 320, 317.1, 435/252.3, 252.33; 536/27

[56] References Cited

U.S. PATENT DOCUMENTS 4,464,473  8/1984  Orser et al. .................... 435/172.3
4,468,464  8/1984  Cohen et al. .................... 435/320

OTHER PUBLICATIONS

Verstreate et al., 1984, Infec. and Immun. 46, 182–187.
Winter et al., 1983 Infec. and Immun. 42, 1159–1167.
Bolivar F., 1978 Gene 4, 121–136.

*Primary Examiner*—Charles F. Warren
*Assistant Examiner*—Christopher S. F. Low
*Attorney, Agent, or Firm*—Tilton, Fallon, Lungmus & Chestnut

[57] ABSTRACT

A gene of *Brucella abortus* encoding a novel 31,000 dalton immunogenic protein has been isolated and introduced into synthetic recombinant DNA molecules. A plasmid containing the gene sequence also contains a promoter sequence for expression of the gene.

2 Claims, 1 Drawing Sheet

TRANSFORMED PLASMID pBR325 (BCSP-I) CONTAINING GENE FOR BRUCELLA ABORTUS PROTEIN BCSP-3I

RECOMBINANT *BRUCELLA ABORTUS* GENE EXPRESSING IMMUNOGENIC PROTEIN

RELATED APPLICATION

This application is a continuation-in-part of co-pending application Ser. No. 06/905,297, filed Sept. 8, 1986, now abandoned.

FIELD OF INVENTION

This invention relates to immunogenic proteins of *Brucella abortus*. More particularly, the invention relates to the isolation and identification of a gene of *B. abortus*, and the incorporation of the isolated gene in a recombinant DNA molecule to express an immunogenic protein.

BACKGROUND OF INVENTION

Bovine brucellosis is a disease associated with abortions and infertility, and is caused by the gram-negative organism *Brucella abortus*. Despite an active vaccination program, bovine brucellosis continues to be a problem in the United States (10, 16) and is an economically important disease. Numerous recent reports have been published on various vaccines for the prevention of experimental brucellosis in laboratory animals and cattle. These vaccines include live, reduced dose vaccines (1, 7, 25), nonviable whole cell vaccines (9, 11, 26, 27), cell-free detergent extracts (4, 5, 8, 13), phenol extracts (2, 18, 19), and ribosomal preparations (17). Some of the preparations, in particular, the detergent-extractable protein-peptidoglycan fraction, provide durable immunity in mioe and young cattle, but were less efficacious in adult cattle (6). Inclusion of adjuvants such a trehalose dimycolate (TDM) and muramyl dipeptide (MDP) has been shown to enhance the efficacy of some bacterins (26). The use of complex heterogeneous o killed-cell vaccines often results in the production of undesirable granulomas and undesirable long-lasting serum antibody titers which interfere with the diagnostic tests used for bovine brucellosis. This latter problem is also occasionally encountered with live vaccines. Nonviable vaccines are desirable, since the live attenuated vaccine strain can cause mammary gland infections and also abortions in adult vaccinated cattle. However, many of the heterogeneous multicomponent vaccine preparations such as lipopolysaccharides (LPS) and proteins may result in antagonistic immune responses to the vaccine (6). To avoid these problems, it is preferable to develop vaccine preparations which are biochemically homogeneous. One approach to this goal has led to the development of a method (20) for the isolation of a fully soluble and stable protein preparation (BCS protein) from *Brucella abortus* strain 19.

It has been previously shown that a mixture of proteins can be removed from the surface of methanol-inactivated *Brucella abortus* cells by aqueous hypertonic sodium chloride-sodium citrate (20). Such a protein mixture isolated from an attenuated *Brucella abortus* strain was immunogenic in both rodents and appeared to be immunogenic in cattle. One of the proteins, having a molecular weight of around 30,000, was purified by chromatofocusing on a PBE column developed with a descending pH gradient from pH 6.2 to 4.0. The purified protein was found to be a more effective immunogen in lemmings than the total multicomponent extract (25). However, the isolation procedure employed (i.e., chromatofocusing) did not permit recovery of the protein in sufficient quantity for use in preparing an antiserum.

As described in Tabatabai, et al. (1979, Ref. 20) the washed methanol-inactivated cells were resuspended in 1 M NaCl-0.1 M sodium citrate and agitated with glass beads in a tissue disintegrator. The protein in the supernatant thus obtained was precipitated with ammonium sulfate to obtain the protein mixture. Polyacrylamide gel electrophoresis indicated the presence of a protein of approximate molecular weight of 30,000 daltons (Ref. 20, FIG. 4, p. 674), but the procedure was not practical for use in preparing antiserum to the protein.

It has been suggested that soluble salt-extractable proteins from *Brucella abortus* may be of potential value for preparing vaccines and/or for use as diagnostic agents in the prevention or diagnosis of bovine brucellosis (Tabatabai, et al., 1984, Ref. 22). Further, the salt-extractable proteins of *Brucella abortus* have been analyzed by crossed immuno-electrophoresis using rabbit antiserum protein antigens and by isoelectric focusing with polyacrylamide gels Tabatabai, et al. 1984, Ref. 23). The isoelectric pH's of the extracted proteins were profiled in FIG. 4, page 557, of Ref. 23.

SUMMARY OF INVENTION

The *Brucella abortus* gene coding for a protein, referred to herein as BCSP-31, has been isolated and identified. The protein expressed by the BCSP-31 gene has a molecular weight of approximately 31,000 daltons, and reacts with antiserum prepared to the Brucella 31,000-dalton protein. The BCSP-31 gene was cloned in a bacteriophage vector and incorporated in plasmid expression vectors. The isolated DNA sequence containing the gene also included a control sequence for the gene which amplifies its expression.

The BCSP-31 gene can be employed to produce the BCSP-31 protein, which can be used in the preparation of vaccine for prevention of *Brucella abortus* and/or as a diagnostic reagent to identify cattle which have been infected. If cattle have been vaccinated with an immunogen which does not contain the BCSP-31 protein, the protein can be employed as a diagnostic agent to distinguish between animals which have had a natural infection and those which have been vaccinated.

To confirm the identity of the isolated gene, a new procedure was developed for preparing and recovering sufficient pure BCSP-31 protein from *Brucella abortus*. Instead of subjecting the cells suspended in the sodium chloride-sodium citrate solution to the action of a tissue disintegrator, an entirely different treatment was used. Specifically, the suspension was heated in a water bath at 60° C. for 16 hours, then cooled, and centrifuged to separate the solids from the protein-containing supernatant. The work-up procedure for obtaining the BCSP-31 protein from this new type of supernatant is later described herein. The purified BCSP-31 protein obtained was used to prepare an antiserum which was employed for positive identification of the BCSP-31 gene.

THE DRAWING

The accompanying drawing illustrates a recombinant DNA plasmid containing the BCSP-31 gene together with a control sequence. The circular plasmid pBR325 (BCSP-31) is show in linear form for convenience of reference. Key endonuclease restriction sites are indicated.

DEPOSIT INFORMATION

Viable cultures of *E. coli* transformed with the plasmid pBR325 (BCSP-31) have been placed on permanent deposit for U.S. patent purposes with the American Type Culture Collection, 12301 Parklawn Drive, Rockville, Md., 20852. The deposited culture was identified by the designation pBR325 (BCSP-31) and has been assigned ATCC Accession No 67190.

DETAILED DESCRIPTION

Figure 1:
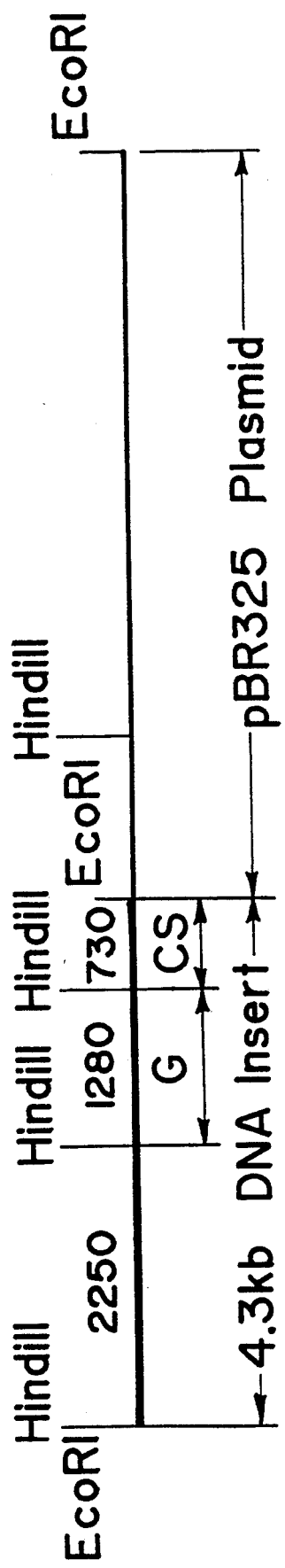

This invention comprises a synthetic recombinant DNA molecule containing a DNA sequence comprising a gene of *Brucella abortus* which expresses an immunogenic protein having a molecular weight of approximately 31,000 daltons (31,000±1,000). The molecular weight refers to determination with sodium dodecyl sulfate (SDS) polyacrylamide gel electrophoresis under denaturing conditions.

In a preferred embodiment, the DNA molecule comprises a plasmid which is capable of transforming bacteria. For example, the plasmid may be used to transform *E. coli* providing an expression vector for the BCSP-31 protein. Many different strains of *E. coli* are suitable vectors, such as, for example, HB101. This protein is further characterized by having an isoelectric point of around 4.9. The first 25 amino acids of the protein have been sequenced as a further identification.

In preferred embodiments, the plasmid DNA insert not only includes the sequence for the BCSP-31 gene but also a DNA sequence which comprises a control sequence for the gene, and which functions to amplify the expression of the protein. Such an expression vehicle is diagrammatically illustrated in FIG. 1. Into the known plasmid pBR325 there has been inserted a 4.3 kilobase (kb) segment of DNA isolated from *Brucella abortus*. The 1.28 kb DNA segment "G" contains the sequences coding for the BCSP-31 gene, while the 0.73 kb DNA segment "CS" contains a control sequence for the gene.

This recombinant DNA invention is further illustrated by the following examples.

EXAMPLE I

Isolation of Protein

Washed methanol-inactivated and attenuated strain of *B. abortus* (Strain 19) cells were suspended in 1M sodium chloride—0.1 M sodium citrate, pH 7.9, as described previously (Tabatabai, et al., 1979, Ref. 20). *Brucella abortus* strain 19 is produced and maintained by the U.S. Department of Agriculture, Animal and Plant Health Inspection Service, Science and Technology, National Veterinary Services Laboratories, P.O. Box 844, Ames, Iowa, 50010. Using a new procedure, the suspension was heated in a waterbath at 60° C. for 16 hr., then cooled to 5° C. and centrifuged at 12,000×g for 20 min. The pelleted solids were discarded. The resulting protein-containing supernatant was dialyzed against 5 mM ammonium bicarbonate until the dialysis solution tested negative for chloride ion. The protein solution was then concentrated by lyophilization, and resuspended in a small volume (1 ml) of 5 mM ammonium bicarbonate. Protein concentration was determined as previously described (Tabatabai, et al., 1979, Ref. 20). Two ml (5.0 mg) of the protein solution were dialyzed against 50 mM ammonium acetate pH 4.3, then centrifuged at 12,000×g for 10 min. The purified protein solution (2.5 mg) was applied on a column containing carboxymethyl cellulose (CM32, Whatman). The bed volume was 10 ml in a 1 cm dia. by 12.7 cm high column. Adsorbed protein was eluted with a 200 ml linear gradient of 0 to 1 M sodium chloride in 50 mM ammonium acetate pH 4.3. Elution of protein was monitored by measuring absorbance at 280 nm. The protein eluting between 0.1 and 0.15 M was pooled, dialyzed against 5 mM ammonium bicarbonate, and concentrated by lyophilization.

The isolated protein, designated BCSP-31, had an isoelectric point (pI) of 4.9 and a molecular weight of approximately 31,000 daltons (±1000) as determined by SDS gel electrophoresis using sodium dodeoyl sulfate under denaturing conditions. The first 25 amino acids of BCSP-31 from the amino-terminal end have been determined as Gln-Ala-Pro-Thr-Phe-Phe-Arg-Ile-Gly-Thr-Gly-Gly-Thr-Ala-Gly-Thr-Tyr-Tyr-Pro-Ile-Gly-Gly-Leu-Ile-Ala, wherein Gln, Ala, Pro, Thr, Phe, Arg, Ile, Gly, Tyr, and Leu, respectively, represent glutamine, alanine, proline, threonine, phenylalanine, arginine, isoleucine, glycine, tyrosine, and leucine.

EXAMPLE II

Antisera were produced in rabbits using the 31 kilodalton protein prepared as described in Example I at a concentration of 100 µg per ml of sterile saline. An equal volume of Freund's incomplete adjuvant was added, and the mixture was homogenized in a 5-ml syringe. Injections were given intradermally with 0.2 ml quantities at multiple sites dorsocranially. Injections were given at two-week intervals for six weeks. The last injection of the 31 kilodalton protein without Freund's adjuvant was given intravenously one week before exsanguination. The specificity of the antiserum was tested by crossed immunoelectrophoresis according to the procedure described by the manufacturer of the immunoelectrophoresis equipment, and as published by Tabatabai, et al., 1984, Ref. 23.

EXAMPLE III

Development of Clone Library

*Brucella abortus* DNA was purified from *Brucella abortus* strain 19 cells which had previously been killed by soaking in 60% methanol at 4° C. for 4 hours. The killed cells were removed from the methanol solution by centrifugation and resuspended at a ratio of 10 ml per gram of cells in 50 mM glucose, 10 mM ethylenediaminetetraacetic acid, 2 mM tris(hydroxymethyl)-aminomethane, pH 7.5. 10 mg of chicken egg white lysozyme was added per 10 ml of cell solution and the mixture incubated at room temperature for 30 minutes. One tenth volume of 20% sodium dodecyl sulfate was then added and the solution mixed until uniform. The solution was then phenol extracted four times and the DNA collected by precipitation with 70% ethanol. The precipitated DNA was dissolved in one half the original volume of 0.01 M tris(hydroxymethyl) aminomethane, pH 8.0, incubated with 50 micrograms/ml of RNAase A for 30 minutes at room temperature, phenol extracted twice more, and reprecipitated from 70% ethanol. The purified DNA was resuspended at a concentration of 1 mg/ml in TE buffer (0.001 M ethylenediaminetetraacetic acid, 0.01 M tris(hydroxymethyl) aminomethane, pH 7.5).

A library of *Brucella abortus* DNA sequences was created by the partial cleavage of purified Brucella DNA with the restriction endonuclease Sau3A. The resultant DNA fragments were fractionated by centrifugation on a 5 to 20% sucrose gradient made in 1M sodium chloride. Fractions were collected and concentrated by ethanol precipitation. Each fraction was resuspended in 1/10 volume of TE buffer and the size range determined by 0.5% agarose gel electrophoresis in TBE buffer [0.089 M Tris(hydroxymethyl) aminomethane, 0.089 M boric acid, 0.01 M ethylenediamine-tetraacetic acid] with bacteriphage lambda DNA cut with restriction endonuclease Hind III as a standard. DNA fragments in the 15-20 kb range were ligated into bacteriophage lambda 1059 DNA (Karn, et al., 1980, Ref. 12) with $T_4$ DNA ligase. The lambda 1059 DNA had previously been cut with restriction endonuclease BamH. The resultant recombinant lambda DNA was packaged in vitro using a packaging kit purchased from Promega Corp., and amplified by plating on agar plates (Maniatis, et al., Ref. 15).

The library was screened with rabbit antisera directed against the multicomponent Brucella high salt protein extract (BCS proteins). The preparation of this antisera was described in Example II. The screening procedure involved the adherence of proteins from individual plaques to nitrocellulose paper, incubation with the rabbit antiserum, and a second incubation with either radioactively labelled protein A or horseradish peroxidase conjugated to goat anti-rabbit IgG serum fraction being similar to the procedures previously described.

EXAMPLE IV

Isolation of Gene

Characterization of the protein products of each positive clone revealed one clone which produced a 31 kilodalton protein which reacted strongly with anti-Brucella antisera in the Western blot procedure (Towbin, et al., 1979, Ref. 24). This recombinant lambda bacteriophage clone contained approximately 20 kb (20,000 base pairs) of Brucella DNA. This DNA was purified, cut with the restriction endonuclease EcoR1 and the resultant DNA fragments inserted into lambda gt (Wes) - lambda B (Leder, et al., 1977, Ref. 14). The resultant clones were screened as described above, and positive clones identified. Each positive clone contained a 4.3 kb insert of Brucella DNA. This 4.3 kb DNA fragment was then subcloned into the unique EcoR1 sites of the plasmids PKK223-3, obtained from Pharmacia P-L Biochemicals, Inc., Milwaukee, WI and pBR325 (Bolivar, 1978, Ref. 3). Expression of the 32 kilodalton Brucella protein, as detected by the Western blot procedure, was found from both plasmids, and is independent of the orientation of the Brucella DNA fragment. These plasmids were respectively designated pKK223-3(BCSP-31) and pBR325(BCSP-31). All of the above plasmids were selected with 50 micrograms/ 1 of ampicillin.

EXAMPLE V

Identification of Gene

The reagent used was the specific antiserum prepared as described in Example II, being antiserum against the highly purified 31 kilodalton protein (BCSP-31) prepared as described in Example I. The antiserum was found to react strongly with the 31 kilodalton protein produced by the E. coli clones pKK223-3(BCSP-31) and pBR325(BCSP-31). Subclones containing only the 1.28 kb (fragment G in FIG. 1) HindIII fragment also produce the 31 kilodalton protein but at a 20-fold lower yield. When the 1.28 kb DNA fragment is reunited with the 0.73 kb HindIII fragment in the original orientation, the original level of protein production is restored. These results indicate that the protein coding sequences are located on the 1.28 kb fragment, and that important control sequences amplifying the expression of the gene are located on the 0.73 kb fragment. The gene is therefore under control of its own promoters. It has also been found that in several different media and with two different host strains of E. coli that the 31 kilodalton protein is partially excreted into the growth medium. This unusual property presumably is dictated by nucleotide sequences located within the protein coding region and also within the gene regulatory sequences.

EXAMPLE VI

Depositing of Transformed E. coli

An E. coli clone (HB101) transformed with the plasmid pBR325(BCSP-31) has been placed on deposit with the American Type Culture Collection, Rockville, MD. The culture is identified as E. coli strain pBR325(BCSP-31) and by the ATCC Accession No. 67190. The deposited strain will be available pursuant to all requirements of the United States Patent and Trademark Office. The plasmid of the deposited strain was prepared as described in Example IV and identified as described in Example V. In addition to the gene producing the BCSP-31 protein, the plasmid contains the control sequences for expression of the protein. pBR325 is derived from pBR322 as described by Bolivar (1978), Ref. 3.

A linear diagram of the recombinant plasmid pBR325(BCSP-31) is shown in FIG. 1. It will be understood that the EcoR1 site shown at each end of the linear representation is actually the same site in the circular form of the plasmid. The EcoR1 and HindIII restriction sites are indicated. The gene sequences coding for the BCSP-31 protein are located in the 1.28 kb segment between two Hind III sites of the DNA insert, and the control sequences for the BCSP-31 gene are located in the 0.73 kb segment between a HindIII site on the insert and an EcoR1 site of the pBR325 plasmid.

REFERENCES

1. Alton, G.G. and Corner, L.A., 1981, *Aust. Vet. J.*, 57:548-550.
2. Bascoul, S., Cannat, A., Huguet, M.F., and Serre, A., 1978, *Immunol.*, 35:213-221.
3. Bolivar, F., 1978, *Gene*, 4:121-136.
4. Bosseray, N., 1978, *Brit. J. Exp. Pathol.*, 59:354-365.
5. Bosseray, N. and Plommet, M., 1980, *Ann. Microbiol. (Inst. Pasteur)*, 131A:157-169.
6. Bosseray, N., Plommet, M., and Dubray, G., 1978, *Ann. Microbiol. (Inst. Pasteur)*, 129B:571-579.
7. Deyoe, B.L., Dorsey, T.A., Meredith, K.B., and Garrett, L., 1979, *Proc. 83rd Annual Meet. U.S. Anim. Health Assoc.*, p. 92-104.
8. Ellwood, D.C., Keppie, J., and Smith, H., 1967, *Brit. J. Exp. Pathol.*, 48:28-39.
9. Foster, J.W. and Ribi, F., 1962, *J. Bacteriol.*, 84:258-268.
10. Gillespie, J.H. and Timoney, J.F., 1981, "*Brucella bortus*", p. 127-137, in J.H. Gillespie and J.F. Timoney (eds), *Hagan and Bruners' Infectious Diseases of Domestic Animals*, 7th ed., Cornell University Press, Ithaca, N.Y.

11. Jones, L.M. and Berman, D.T., 1971, *J. Infect. Dis.*, 124:47–57.
12. Karn, J., et al. (1980), *Proc. Nat. Acad. Sci.*, 77:5172–5176.
13. Keppie, J.K., Witt, K., and Smith, H., 1972, *Brit. J. Exp. Pathol.*, 53:518–528.
14. Leder, P., et al. (1977), *Science*, 196:175–177.
15. Maniatis, T., et al. (1982), *"Molecular Cloning, A Laboratory Manual"*, pp. 260–268 and 293–294. Cold Spring Harbor Press, Cold Spring Harbor.
16. Nicoletti, P., 1983, *Dev. Biol. Stand.*, 31:129–135.
17. Phillips, M. and Deyoe, B.L., 1981, *Vet. Microbiol.* 6:95–106.
18. Rasooly, G., Olitzki, A.L., and Sulitzea, D., 1966, *Israel J. Med. Sci.* 2:569–584.
19. Renoux, G., Renoux, M., and Tinelli, R., 1973, *J. Infect. Dis.* 127:139–148.
20. Tabatabai, L.B., Deyoe, B.L. and Ritchie, A.E., 1979, *Infect. Immun.* 26:668–679.
21. Tabatabai, et al. (1983), *Fed. Proc.*, 42:2127.
22. Tabatabai, et al. (1984), in *"Develop. Biol. Standard"* Vol. 56, pp. 199–211 (S. Karger, Basel), presented 3rd Intern. Symp. on Brucellosis, Algiers, Algeria, 1983.
23. Tabatabai, et al. (1984), *Vet. Microbiol.* 9:549–560.
24. Towbin, et al. (1979), *Proc. Nat. Acad. Sci. (USA)*, 76:4350–4354.
25. Woodard, L.F. and Tasman, R.L., 1983, *Am. J. Vet. Res.* 44:907–910.
26. Woodard, L.F., Toone, N.M., and McLaughlin, C.A., 1980a, *Infect. Immun.* 30:409–412.
27. Woodard, L.F., Toone, N.M., and McLaughlin, C.A., 1980b, *Can. J. Comp. Med.* 44:456–458.

We claim:

1. A synthetic recombinant DNA molecule containing a DNA sequence consisting essentially of a gene of *Brucella abortus* encoding an immunogenic protein having a molecular weight of approximately 31,000 daltons as determined by sodium dodecyl sulfate polyacrylamide gel electrophoresis under denaturing conditions, said protein having an isoelectric point around 4.9, and containing a twenty-five amino acid sequence from its amino terminal end consisting of Gln-Ala-Pro-Thr-Phe-Phe-Arg-Ile-Gly-Thr-Gly-Gly-Thr-Ala-Gly-Thr-Tyr-Tyr-Pro-Ile-Gly-Gly-Leu-Ile-Ala, wherein Gln, Ala, Pro, Thr, Phe, Arg, Ile, Gly, Tyr, and Leu, respectively, represent glutamine, alanine, proline, threonine, phenylalanine, arginine, isoleucine, glycine, tyrosine, and leucine.

2. The synthetic recombinant DNA molecule of claim 1 consisting essentially of said gene as contained in the plasmid vector deposited with the American Type Culture collection as transformed *E. coli* strain pBR325 (BCSP-31) under accession number 67190, which vector includes a *Brucella abortus* promoter for expression of said gene.

* * * * *

UNITED STATES PATENT AND TRADEMARK OFFICE
CERTIFICATE OF CORRECTION

PATENT NO. : 5,023,174

DATED : June 11, 1991

INVENTOR(S) : Mayfield et al.

It is certified that error appears in the above-identified patent and that said Letters Patent is hereby corrected as shown below:

On the Title Page, Item [73] should read:

Assignees: Iowa State University Research Foundation, Ames, Iowa; The United States of America as represented by the Department of Agriculture.

Signed and Sealed this

Fourteenth Day of January, 1992

Attest:

HARRY F. MANBECK, JR.

Attesting Officer      Commissioner of Patents and Trademarks